United States Patent [19]

Russier

[11] Patent Number: 4,728,331
[45] Date of Patent: Mar. 1, 1988

[54] ENDO-EXTRACORPOREAL IMPLANT AND FIBRO-INDUCTIVE AND/OR OSTEO-INDUCTIVE SEAL THEREFOR

[76] Inventor: Jean-Jacques Russier, 11 avenue Champ de Mars, Valence (Drome), France

[21] Appl. No.: 770,685

[22] Filed: Aug. 29, 1985

[30] Foreign Application Priority Data

Aug. 31, 1984 [FR] France ................ 84 13947

[51] Int. Cl.⁴ ................ A61F 2/28; A61C 8/00
[52] U.S. Cl. ................ 623/16; 433/175; 433/201.1; 106/35
[58] Field of Search ........... 433/201.1, 175; 623/16; 106/35, 161; 260/998.11; 424/95; 514/21, 801; 523/115; 524/17, 21

[56] References Cited

U.S. PATENT DOCUMENTS

| | | | |
|---|---|---|---|
| 3,934,347 | 1/1976 | Lash et al. | 433/201.1 X |
| 4,051,598 | 11/1977 | Sneer | 433/201.1 X |
| 4,172,128 | 11/1979 | Thiele et al. | 424/95 |
| 4,379,694 | 4/1983 | Riess | 433/201.1 |
| 4,440,750 | 4/1984 | Glowacki et al. | 424/95 |
| 4,444,206 | 4/1984 | Gold | 128/784 |

Primary Examiner—Richard J. Apley
Assistant Examiner—Alan W. Cannon
Attorney, Agent, or Firm—Karl F. Ross; Herbert Dubno

[57] ABSTRACT

A physiological joint of dental material is provided around an implant for dental or nondental purposes as a fibro-inductor or osteoinductor promoting growth from surrounding tissue to bond the implant in the organism while preventing incursion of bacteria.

6 Claims, 4 Drawing Figures

FIG_3
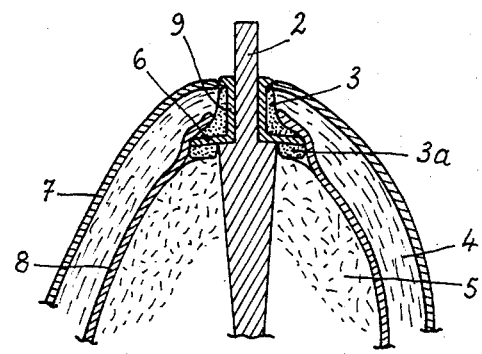
FIG_4
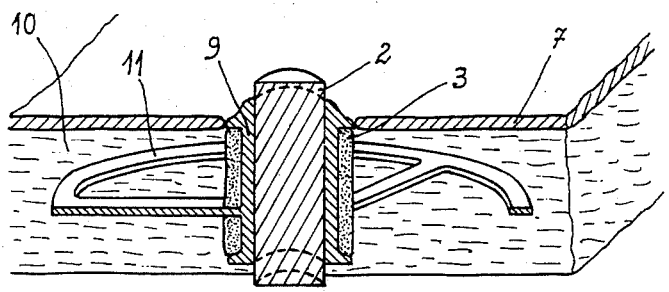

ENDO-EXTRACORPOREAL IMPLANT AND FIBRO-INDUCTIVE AND/OR OSTEO-INDUCTIVE SEAL THEREFOR

FIELD OF THE INVENTION

The present invention relates to a seal or joint for an endo-extracorporeal implant providing a mechanical connection between the implant and the surrounding tissue.

BACKGROUND OF THE INVENTION

It is well known that the provision of endo-extracorporeal implants in tissue of the human body involves many problems, apart from questions of rejection which are engendered whenever a foreign body is introduced into an organism. The problems increase when this body is not only in contact with tissues of the organism in which the implant is provided but is also in contact with the external milieu.

For example, where the implant traverses the tissue or emerges therefrom into the external milieu, sites are provided which can allow or encourage the entry of bacteria, the bacterial action at the regions surrounding the implant causing a progressive epithelial invagination along the implant so that the implant becomes progressively separated from healthy tissue around it.

This problem has been recognized in the past and it has been proposed to provide bacterial barriers or seals around the implant which are intended to prevent just this type of isolation of the implant by the action of microorganisms.

In U.S. Pat. No. 3,663,965, for example, a percutaneous device is described which is designed to permit the passage of a wire or tube through the skin. In this case, a sealing barrier is provided against bacterial incursion from Teflon, silicone, rubber, polypropylene, polyurethane, an epoxy or by various forms of pyrolyzed carbon.

Such systems have not been found to be fully effective and the epithelial invagination may occur in any event around the barrier which is provided. The entire structure is retained only by virtue of epithelial colonization which gives rise to microscopic perforations of the support. The perforations tend to slow the development of bacteria in the space between the epithelium and the foreign body, a space which cannot be cleansed free from the bacteria in any practical manner.

The European patent No. EP-A 0,039,189 describes a hypodermic apparatus which comprises a pin whose upper portion is formed with a knob, which, like the lower knob, is constituted of expanded polytetrafluoroethylene whose microstructure is intended to permit three-dimensional tissue penetration. The pin, however, has an inert character. The growth of tissue into or in contact with this body is therefore comparatively slow.

OBJECTS OF THE INVENTION

It is, therefore, the principal object of the present invention to provide an implant and a method of making same and sealing same in the organism which allows the bonding of the implant to the surrounding tissues including osteal, gingival or cutaneous tissue and which eliminates or reduces any tendency for bacterial penetration and promotes rapid mechanical anchoring of the implant to the surrounding tissues.

Another object of the invention is to obviate the drawbacks of the earlier techniques described above.

SUMMARY OF THE INVENTION

These objects and others which will become apparent hereinafter are attained, in accordance with the invention, by providing a physiological seal between the implant and surrounding tissue which is fibro- and/or osteo-inductive, i.e. capable of promoting the growth of connective tissue and bone tissue into bonding or attaching relationship to the implant and thus ensuring firm anchorage of the implant in the surrounding connective and/or osteal tissue in which the implant or against which the implant is seated.

According to the invention, at the interface between the implant and the tissue in which the implant is to be anchored, I provide the physiological point of an attachment material of dental orgin, namely, dentin, dentin organic matrix, enamel or its organic matrix or a combination thereof.

In other words, I have discovered that in spite of the fact that efforts to reseat dental components such as lost teeth have generally been found to be fruitless, certain dental materials namely dentin, its organic matrix and enamel and its organic matrix have the characteristic that they can act as fibro- and/or osteo-inductors which either initiate growth of or permit attachment of neighboring connective tissue and/or oseos tissue to an implant where the dental material is located in an interface between this implant and the surrounding tissue.

With the system of the invention, a fibrous attachment is formed between the implant and the surrounding connective tissue which eventually is calcified, the fibers being substantially continuous with the new joint forming material, i.e. the dentin, enamel or the organic matrix structures thereof. This organization of the tissue adjoining the implant is sufficient to preclude epithelial invagination around the implant and thus avoid the formation of bacterial pockets which might cause a separation of the implant from the supporting structure so that an effective transition is provided between the implant and the mucous or continuous tissues therearound.

The continuity of fibrous structures seems to be the most efficient means for retaining the implant available to the organism.

As noted earlier, the material promoting attachment is dentin or its organic matrix. However, in the case of an ordinary osteo implant the joint can be two fold, one attachment promoting material being primarily a fiber inductor with respect to the connective tissue while the other is primarily an osteo-inductor for the periosteum. Thus, where the implant interface with the fibrous-connective tissue is provided, the material can be dentin or its organic matrix while in the periosteal region of the bone/implant interface the material is dental enamel or its organic matrix.

It has been found to be important to avoid direct contact between the dentin and the bone and for this purpose we may provide between the bone and the dentin a layer of barrier material, for example, a biologically compatible metal or alloy, a bioceramic, vitrified carbon or a biocompatible polymer. Whenever an osteo-inductor is required, I prefer to use dental enamel or its organic matrix.

In the case of a juxtaoseos implant which is in contact with the periosteum, the connection can be made between the organic matrix of dentin and the periosteum and, even, if it is absent, the mucous fiber.

BRIEF DESCRIPTION OF THE DRAWING

The above and other objects, features and advantages of the present invention will become more readily apparent from the following description, reference being made to the accompanying highly diagrammatic drawing in which:

FIG. 3 is a similar to FIG. 2 illustrating an embodiment which enables control of the level of the sealing material or its renewal without necessarily having the latter directly on the implant; and FIG. 4 is a perspective partially sectional view showing the application of the invention to a transcutaneous implant.

SPECIFIC DESCRIPTION

Figure 1:
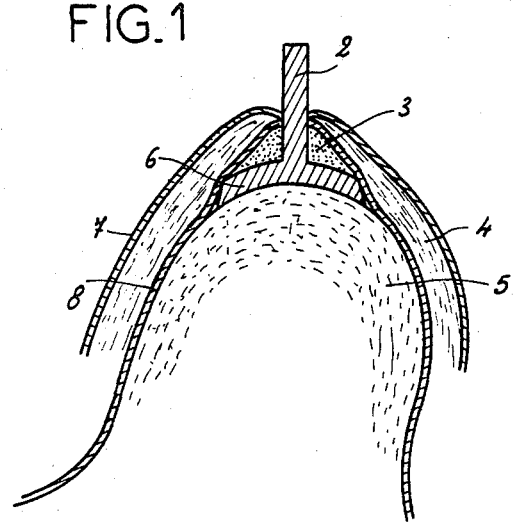
FIG. 1 is a transverse section of a juxtaoseos dental implant having a single post adapted to anchor a dental prothesis and covered with a physiological interface material or joint adapted to form a seal according to the invention.

In the drawing, I have used the reference numeral 2 generally to represent the implant and the reference numeral 3 to represent a physiological seal according to the invention.

While the seal in any particular figure may be described as being formed by one of the sealing compositions within the scope of this invention, it should be understood that the other sealing materials may be equally used in each embodiment.

Figure 2:
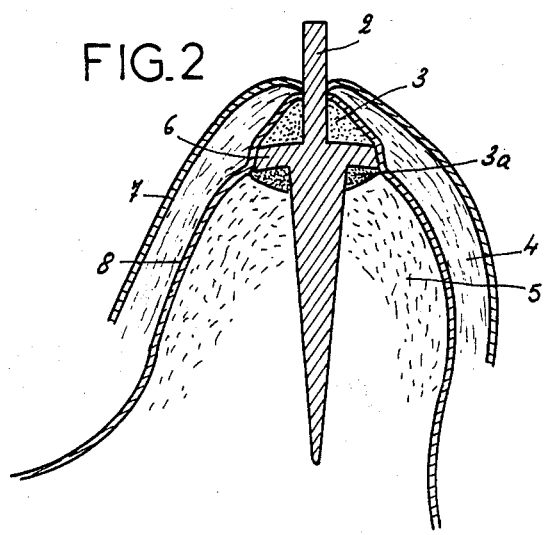
FIG. 2 is a view similar to FIG. 1 showing an endoseos implant.

In the embodiments shown in FIGS. 1 through 3, the gingival tissue or gum is represented at 4, the bone tissue is represented at 5 and a flange, shoulder or lip projecting laterally from the implant 2 acts as a support for a physilogical joint represented at 5. The gingival epithelium has been diagrammatically shown at 7 and the periosteum at 8.

The physiological joint 3, according to the invention, is constituted from dentin obtained from teeth which have not been exposed to dental plaque and which are preserved in physiological serum at a temperature of about −20° C. This dentin previously decalcified by superficial treatment with citric acid or ascorbic acid is cut into small domed structures of 4 to 5 mm of diameter and provided with a central passage through which the post of the implant passes. Since the posts are of standardized diameters, the dentin dome can be provided with a hole of standard diameter sufficient to clear the post.

To be certain that one can avoid destruction of the dentin by coleoslasts, contact of the dentin with the bone is prevented. It is for this reason that the support flange 6 is provided to space the dentin body from the bone. The flange 6 can be composed of the same material and this can be integral with the post of the implant. If can, however, also be composed of any barrier material, e.g. a metal or metal alloy, bioceramic, vitrified carbon or the like.

In the case of juxtaoseos implant, such as that represented in FIG. 1, the joint-forming or seal-forming member 3 is of relatively simple structure.

However, a double seal or joint is required for the embodiment of FIG. 2 because here the physiological seal has two parts 3 and 3a, the first of which can coat the upper surface of the flange 6 and be of dome shape in the manner described while the part 3a cuts the underside of the flange and is interposed between the flange and the bone 5.

It is constituted by a thin layer of dental enamel, previously treated in the manner described for the dentin, i.e. superficially decalcified. The layer 3a thus forms an osteo-inductor, while the layer 3 is a fibroinductor to produce a tissue interlocked between the bone and the implant on the one hand and the conjunctuous fibrous tissue and the implant on the other hand so that the formation of pockets around the implant is completely precluded.

In the embodiment shown in FIG. 3, the physiological seal 3 is not affixed directly to the implant 2 but is mounted upon a sleeve 9 which can be slidably forced over the implant and secured thereto by any conventional bonding agent capable of adhering to the implant. This sleeve 9 which can be composed of a bioceramic or metal, e.g. the same metal as the implant, can be formed unitarily with the flange 6 supporting the joint 3.

This permits a control of the height of the joint 3 on the implant since the degree to which a sleeve is slide over and bonded to the implant can be selected with ease.

In the case of damage to the physiological seal and thus the need for renewal thereof, or where an implant has been emplaced without the physiological seal, the use of the sleeve permits application of the physiological seal without removal or resetting of the implant.

Such replacement of the seal may be necessary in the case of inflammation, infection or accident in the region of the original physiological seal.

The implant and/or the sleeve can be emplaced by conventional techniques, avoiding epithelial invagination and controlling the epithelium in the region of the application so that with cicatrization the seal will be closely surrounded by the epithelium and the underlying gingival tissue.

The dentin 3 and/or the enamel 3a are cemented sealingly to the support 6 by any noncytotoxic neutral dental adhesive and the region around the implant is sutured to ensure an intimate contact between the periosteum and the dentin.

As a consequence, a physiological seal which is perfectly tight is provided at the point of interruption of the gingival tissue by the implant and the problem of entry of bacteria is eliminated. The implant thus becomes truly attached to the bone and to the tissue which covers the implant, not by means of an epithelial sleeve which evolves around the implant and offers the possibility of chronic infection and drainage but by an actual bond of the physiological joint, i.e. the dentin and enamel materials, with the tissue in contact thereof. The physiological joint constitutes itself a fibroinductor and/or osteoinductor promoting fibrous tissue growth or bone-tissue growth and can be applied not only in the field of dental implants but wherever a perfect seal in the region of interruption of the cutaneous or mucous tissue may be required.

This is demonstrated by FIG. 4 which shows a physiological joint 3 sealed to the surrounding tissue in a transcutaneous application. Here the implant 2 can be a rigid member, such as a wire running to an electrical appliance introduced into the organism or a flexible tube or any other percutaneous or transcutaneous device of autogeneous or heterogeneous orgin. In this case the physiological material forming the joint 3, namely the dentin material, can be fixed on the implant directly or provided, as is preferred, on a sleeve which can be slidable on the implant and fixed secondarily thereto by an appropriate adhesive if desired. This sleeve has been represented at 9 because it can correspond to part 9 of FIG. 3.

The physiological joint 3 can be bonded by an adhesive to the sleeve 9 or anchored between flanges thereof as has been shown in FIG. 4.

When the implant is to be transcutaneous or somewhat supple and to be embedded in the organism at some depth, it has been found to be advantageous to provide it with a stabilization member such as a wing or flange or hoop as represented at 11 to limit the shifting of the sleeve 9 with respect to the tissue in which it is embedded.

If this stabilization wing is incorporated in connective tissue, it should be an openwork structure as shown or be provided with orifices of a flow cross section and number sufficient to permit good vascularization of the most superficial layer.

Preferably, the stabilization wing is formed of a material, e.g. a biocompatible silicone rubber, having a flexibility or suppleness corresponding to that of the tissue which covers it.

Naturally, the invention is applicable to other embodiments than those disclosed and, for example, instead of a shaped solid block forming the physiological joint 3 in the several embodiments, the physiological joint can be formed in agglomerated, compressed or even a somewhat mobile granular or pulverulant mass which can be, if desired, partly enclosed in a biocompatible envelope or membrane.

To improve the fibrous attachment, the physiological joint can be coated with or can incorporate a fibronectin or collagen.

The preparation of the enamel or dentin for the purposes of this invention can involve a superficial decalcification for 3 to 5 minutes with a concentrated citric acid or ascorbic acid aqueous solution at room temperature. When, however, the use of the organic extracellular matrices of the enamel or dentin is preferred, this can be obtained by a prolonged treatment with the same acids. For example, the dentin and enamel may be substantially completely decalcified to the respective matrices by treatment of the enamel or dentin with concentrated aqueous citric or ascorbic acid at a temperature of say 80° C. for 12 to 24 hours.

I claim:

1. A device for implantation in an animal organism having bone tissue covered by connective tissue, said device comprising:

an implant adapted to penetrate into said bone tissue and having a shank extending through said connective tissue and projecting therefrom;

a sleeve affixed to said shank and surrounding same over a portion of the length of said shank within said connective tissue, said sleeve having an outwardly projecting annular flange juxtaposed with said bone tissue; and an annular body of a fibroinductive material of dental origin affixed to and mounted on said sleeve in direct contact with said connective tissue and separated by said flange from said bone tissue.

2. The device defined in claim 1 wherein said annular body is generally of conical shape.

3. The device defined in claim 2 wherein said implant has a spike engaging in said bone tissue and said shank is cylindrical and of a smaller diameter than said spike.

4. The device defined in claim 1 wherein said body is composed of at least one material selected from the group which consists of dentine, dentine organic material, dental enamel and dental enamel organic matrix.

5. The device defined in claim 4 wherein said body further comprises fibronectin or collagen.

6. The device defined in claim 1, further comprising a ring of an osteoinductive material between said flange and said bone tissue.

* * * * *